United States Patent
Wouters et al.

(10) Patent No.: US 8,481,253 B2
(45) Date of Patent: Jul. 9, 2013

(54) CRYOPRESERVATION OF ADIPOSE TISSUE FOR THE ISOLATION OF MESENCHYMAL STEM CELLS

(75) Inventors: Guy Wouters, Putte (BE); Kelly van Wemmel, Londerzeel (BE); Peter de Waele, Lochristi (BE)

(73) Assignee: Cryo-Save AG, Pfaffikon (CH)

( * ) Notice: Subject to any disclaimer, the term of this patent is extended or adjusted under 35 U.S.C. 154(b) by 277 days.

(21) Appl. No.: 12/921,489

(22) PCT Filed: Mar. 19, 2009

(86) PCT No.: PCT/EP2009/053262
§ 371 (c)(1),
(2), (4) Date: Sep. 8, 2010

(87) PCT Pub. No.: WO2009/115581
PCT Pub. Date: Sep. 24, 2009

(65) Prior Publication Data
US 2011/0008300 A1    Jan. 13, 2011

(30) Foreign Application Priority Data
Mar. 19, 2008    (EP) .................................... 08152993

(51) Int. Cl.
*A01N 1/02*    (2006.01)

(52) U.S. Cl.
USPC .......................................................... 435/2

(58) Field of Classification Search
None
See application file for complete search history.

(56) References Cited

U.S. PATENT DOCUMENTS

| | | | |
|---|---|---|---|
| 7,129,035 B2* | 10/2006 | Goldstein et al. | 435/1.3 |
| 7,157,222 B2* | 1/2007 | Khirabadi et al. | 435/1.3 |
| 2009/0305224 A1* | 12/2009 | He et al. | 435/2 |

FOREIGN PATENT DOCUMENTS

| | | |
|---|---|---|
| WO | 03/024215 | 3/2003 |
| WO | 2005/035742 | 4/2005 |

OTHER PUBLICATIONS

Kovalendo et al., "Evaluation of the biological activity of bone marrow preserved by freezing in cold-protective solutions", Meditsinskii Zhurnal Uzbekistana 1970 (2) : 67-69.*
CA abstract of above article AN 73:96432, 1 page, 1970.*
Ardevol et al., "Cooling rates of tissue samples during freezing with liquid nitrogen", J. Biochemical and Biophysical Methods 27 (1) : 77-86 (1993).*
Cui et al., Cryobiology, 55(3):269-278 (2007).
Honadel et al., Cryobiology, 25(4):331-337 (1988).
International Search Report in PCT/EP09/53262, dated Feb. 9, 2010.
Larson et al., Fertility and Sterility, 68(1):143-148 (1997).

* cited by examiner

*Primary Examiner* — Sandra Saucier
(74) *Attorney, Agent, or Firm* — McAndrews, Held & Malloy, Ltd.

(57) ABSTRACT

The present invention relates to a method and composition for the cryopreservation of adipose tissue with the intention to use this tissue in the culturing of stem and/or progenitor cells. The method uses a specific cryoprotection medium to prevent damage of the original tissue during the cryopreservation while still maintaining a high viability of the stem and/or progenitor cells obtained from the cryopreserved adipose tissue. Furthermore the cryoprotection medium of the present invention does not contain any kind of xenogeneic sera, a critical factor since it is the intention of that the cryopreserved tissue is used for obtaining stem and/or progenitor cells that can be used in medicine. The cryoprotection medium is characterized in that it is a solution of physiological water comprising glycerol and sucrose and/or trehalose and optionally serum albumin.

5 Claims, No Drawings

CRYOPRESERVATION OF ADIPOSE TISSUE FOR THE ISOLATION OF MESENCHYMAL STEM CELLS

The present application is filed pursuant to 35 U.S.C. 371 as a U.S. National Phase application of International Patent Application No. PCT/EP09/53262, which was filed Mar. 19, 2009, claiming the benefit of priority to European Patent Application No. 08152993.5, which was filed on Mar. 19, 2008. The entire text of the aforementioned applications is incorporated herein by reference in its entirety.

SUBJECT OF THE INVENTION

The present invention relates to a method for the cryopreservation of adipose tissue with the intention to use this tissue in the culturing of stem and/or progenitor cells. The method uses a specific cryoprotection medium and employs a flat bag system to prevent damage of the original tissue during the cryopreservation while still maintaining a high viability of the stem and/or progenitor cells obtained from the cryopreserved adipose tissue.

PRIOR ART AND TECHNOLOGICAL BACKGROUND

Stem cells retain the ability to renew themselves through mitotic cell division and can differentiate into a diverse range of specialized cell types. Therefore they are considered potentially useful for treatment of a large variety of human and animal conditions. A number of adult stem cell therapies already exist, particularly bone marrow transplants that are used to treat leukaemia and in the future stem cell therapies are anticipated to enable the treatment cancer, Parkinson's disease, spinal cord injuries but also the replacement and repair of tissues such as pancreatic islets, severed nerve cells, skin grafts for burns or abrasions, and haematopoietic cells following chemotherapy and radiation.

Mesenchymal stem and progenitor cells are of great therapeutic potential due to their capacity of self-renewal and multilineage differentiation. They support haematopoiesis and enhance the engraftment of haematopoietic stem cells after co-transplantation. Currently, bone marrow represents the major source of mesenchymal stem and progenitor cells for cell therapy. However, aspiration of bone marrow involves invasive procedures and the frequency and differentiation potential of bone marrow derived mesenchymal stem and progenitor cells decrease significantly with age. Furthermore, the use of bone marrow is not always acceptable due to higher risk for viral infection and the lower number of cells that can be obtained from bone marrow.

Adipose tissue or fat tissue represents an accessible source of stem and progenitor cells, with similar characteristics to bone marrow-derived stem cells. Therefore adipose tissue may be an ideal source of high amounts of autologous stem cells. Adipose tissue derived mesenchymal stem and progenitor cells can for instance be obtained from adipose tissue obtained during liposuction surgery. Since liposuction aspirates are considered as a waste product these liposuction aspirates are a possible source for acquiring adipose tissue derived mesenchymal stem and progenitor cells.

It remains however necessary to preserve these adipose tissues for prolonged periods and cryopreservation is a method for doing such. Cryopreservation is a process where cells or whole tissues are preserved by cooling to low sub-zero temperatures, such as −196° C. At these low temperatures, any biological activity, including the biochemical reactions that would lead to cell death, is effectively stopped. However, appropriate tissue-specific cryoprotection media are required in order to preserve the tissue or cells without causing freezing damage during the approach to low temperatures or warming to room temperature.

The patent application WO03024215 discloses how stem and progenitor cells derived from adipose tissue can be cryopreserved. The proposed method requires the isolation of the stem and progenitor cells from the adipose tissue prior to the cryopreservation. However, these steps are often unnecessary since only a small amount of the cryopreserved samples are actually being used.

Therefore there is a need for a method for cryopreserving adipose tissue under current good manufacturing practices and current good tissue practices, and under conditions that do not affect the biological characteristics of the tissue. When necessary the cryopreserved adipose tissue can subsequently be used for isolating stem and progenitor cells with the intention to use the cells for therapeutic purposes.

Attempts to cryopreserve adipose tissue and separate the stem and progenitor cells after thawing have until now not produced useful amounts of viable stem and progenitor cells.

Furthermore, some methods for cryopreservation and isolation of stem and/or progenitor cells use xenogeneic sera as cryoprotectant or in the cell culture media. These xenogeneic sera, like fetal bovine serum, are a potential source of contaminants, including prions, viruses and mycoplasms, and should therefore be avoided. Furthermore, the high endotoxin content of for instance fetal bovine serum also poses a safety risk. The presence of xenogeneic sera in the culture or cryopreservation of cells have also been found to change expression patterns of genes and induce unstable transcriptional profiles that for instance lead to an overexpression of collagen, changing the adherence characteristics of the cells. Thus cells contacted with a xenogeneic serum or plasma can display significantly different cell expression profiles from cells prior to the contact, and are substantially altered physiologically, functionally and even genetically as a result of the contact with xenogeneic materials.

It is the intention of the present invention to provide a method for the cryopreservation of adipose tissue. The cryopreservation method of the present invention provides a method for the subsequent isolation of a large amount of viable stem and/or progenitor cells from the cryopreserved adipose tissue. The obtained stem and/or progenitor cells can be used for clinical therapies as well as for drug screening or for developing procedures for expansion or differentiation.

SUMMARY OF THE INVENTION

The present invention relates to a method for the cryopreservation of adipose tissue with the intention to use said cryopreserved adipose tissue for the isolation of stem and/or progenitor cells. The isolated stem and/or progenitor cells can be used for therapeutic purposes. In addition, the adipose tissue material can be cryopreserved and stored for later therapeutic use. The invention further relates to a cryoprotection medium for the cryopreservation of said adipose tissue.

In particular, the present invention relates to the preservation of adipose tissue and the subsequent isolation and therapeutic use of cryopreserved adipose-derived stem and/or progenitor cells and matrix materials in therapeutic, structural, or cosmetic applications for repair, reconstitution, and/or reconstruction. Stem and progenitor cells which contain a heterologous gene sequence for use in gene therapy in delivering replacement or novel gene sequences is also contemplated.

In a preferred embodiment the invention provides a cryopreservation method for adipose tissue(s) from which stem and/or progenitor cells can be isolated with a viability of at least 70%.

Because the nature of the stored material, which is not blood, the system of the present invention can be considered as a new tissue banking system allowing the preservation of stem and/or progenitor cells with this high viability which has never been described, or never suggested before with this high viability. Adipose tissue banking is a useful method with a huge potential for regenerative medical applications by isolating and eventually culturing the stem cells after cryopreservation.

The novelty is that the tissue is preserved using a specific freezing technology and this during a long period. The unexpected effect proposed tissue banking system gives rise to a highly valuable frozen tissue from which different stem and/or progenitor cells can be isolated for therapeutic use. Furthermore, the cryoprotection medium of the present invention does not contain any xenogeneic sera. This is especially important since the cryopreserved adipose tissue is used to isolate stem and/or progenitor cells for use in medicine. Xenogeneic sera should be avoided in the cryoprotection medium since the safety and efficacy of xenogeneic sera in diagnostic or other clinical uses has not been established. Furthermore, by not using any xenogeneic sera during cryopreservation of the adipose tissue the risk that the biological characteristics of the cells alter is avoided.

The present invention relates also to the commercial provision of the possibility to store the tissue with a sampling method, logistics and preservation technology.

The invention can also be used for veterinary purpose since there is a parallelism between human adipose tissue and animal adipose tissue.

In a preferred embodiment of the invention, stem and/or progenitor cells obtained from cryopreserved adipose tissue can be used for autologous reconstitution. In a further preferred embodiment, the connective tissue matrix material may be used for autologous or allogenic repair and reconstruction.

The invention also relates to methods of collection, processing, and cryopreservation of the adipose tissue of the present invention.

The present invention also relates to a method for the cryopreservation of adipose tissue with the intention to use this tissue in the culturing of mesenchymal stem cells. The method uses a specific cryoprotection medium and employs a flat bag system to prevent damage of the original tissue during the cryopreservation.

In a particular embodiment the present invention relates to a method according to the invention wherein adipose tissue is cryopreserved in a flat bag using a slow freezing method.

DETAILED DESCRIPTION OF THE INVENTION

The present invention relates in one aspect to methods for the cryopreservation of adipose tissue with the intention to use the cryopreserved adipose tissue in the culturing of stem and/or progenitor cells, should that future need arise for instance for medical reasons such as cellular or tissue repair or regeneration. The invention further relates to a cryoprotection medium and the use thereof for the cryopreservation of adipose tissue.

In the present invention the term "adipose tissue" refers to loose connective tissue composed of multiple cell types including adipocytes and microvascular cells. Adipose tissue includes stem and progenitor cells and endothelial precursor cells. Accordingly, adipose tissue refers to fat including the connective tissue that stores the fat.

In the present invention the term "stem cell" refers to multipotent cells with the potential to differentiate into a variety of other cell types, which perform one or more specific functions and have the ability to self-renewal. Some of the stem cells discussed herein may be pluripotent.

In the present invention the term "progenitor cell" refers to unipotent, bipotent, or multipotent cells with the ability to differentiate into one or more cell types, which perform one or more specific functions and which have limited or no ability to self-renew. Some of the progenitor cells disclosed herein may be pluripotent.

In the present invention the term "viability" refers to the number of living cells based on the presence of DNA and an intact cell membrane system. The viability can be measured by any methods known in the art and for instance using a tryptan blue internalization test or by measuring propidium iodide uptake.

In the present invention the term "processed lipoaspirate" is regarded as adipose tissue obtained by processing liposuction aspirates. The processing of the liposuction aspirates is done by equilibrating the liposuction aspirate for a period of approximately 30 minutes until three phases are formed: an oil layer, a processed lipoaspirate fraction and a liposuction aspirate fluid fraction. The liposuction aspirate fluid fraction contains most of the liquids that have been injected during the liposuction procedure. It comprises for instance water, anaesthetics or drugs that constrict the blood vessels and prevent bleeding during the liposuction procedure. The processed lipoaspirate fraction contains the active cellular components of the adipose tissue and therefore this fraction should be regarded as the adipose tissue.

In the present invention the term "container" for the cryopreservation of the adipose tissue refers to a storage system capable of holding a liquid. The container can be in the form of a tube or a collection bag. The collection bags are also referred to as flat bags.

The present invention further relates to stem and/or progenitor cells obtained from adipose tissue that has been cryopreserved according to a method of the invention. When referring to stem and/or progenitor cells in the present invention these cells may preferentially be chosen from the group comprising mesenchymal stem and/or progenitor cells, endothelial stem and/or progenitor cells, epithelial stem and/or progenitor cells and muscle stem and/or progenitor cells, and more preferably mesenchymal stem and/or progenitor cells.

Until the filing of the present application there has been neither a description nor suggestion towards the development of a cryopreservation method for adipose tissue or a method wherein stem and/or progenitor cells, preferably mesenchymal stem and/or progenitor cells, are isolated from cryopreserved adipose tissue. Furthermore, the inventors found surprisingly that by following the method and cryoprotection medium of the present invention, stem and/or progenitor cells, preferably mesenchymal stem and/or progenitor cells, with a high viability are recovered from cryopreserved adipose tissue.

The invention provides a cryopreservation method for adipose tissue. When required the cryopreserved adipose tissue can be thawed and used to isolate stem and/or progenitor cells with a viability of at least 70%. The stem and/or progenitor cells, preferably mesenchymal stem and/or progenitor cells, obtained from the cryopreserved adipose tissue can be used for therapeutic use.

Because the nature of the stored material, which is not blood, the system of the present invention can be considered as a new tissue banking system allowing the preservation of adipose tissue from which stem and/or progenitor cells with this high viability can be isolated. The high viability that can be obtained by the method of the present invention has never been described, or never suggested before. Adipose tissue banking is a useful method with a huge potential for medical applications, preferably regenerative medical applications, by isolating and eventually culturing the stem and/or progenitor cells after cryopreservation.

Since it has already been demonstrated that the number and capacity of stem and progenitor cells decline with age, it is not unreasonable for individuals to bank adipose tissue with the intention to use the cryopreserved adipose tissue for the isolation of stem and/or progenitor cells. This way the individuals have a source of stored, viable, young stem cells available to them if and when they need them as they grow older. Various different disease states where delivery of stem and/or progenitor cells, and for instance the delivery of mesenchymal stem and/or progenitor cells, is likely to be medically beneficial include, but are not limited to bone defects, osteoporosis, myocardial infarction, bone fracture, cartilage damage through accident or arthritis, neurological damage or disease, vascular ischemia, coronary artery disease, chronic skin wounds, osteogenesis imperfecta, and aesthetic or trauma related plastic surgical applications. This list is not intended to limit the utility of the invention as there are numerous medical conditions where stem cell and/or progenitor cell delivery is beneficial, and new applications thereof are being discovered daily. The advantage of banked adipose tissue from which stem and/or progenitor cells can be isolated, include the fact that as autologous cells they carry no risk of introduction of a transfusion or transplant-related disease and there is no risk of rejection or graft versus host disease, which are significant risks for allogenic cells. Furthermore, the application of autologous cells is considerably more efficient than that of cells derived from another person and many-fold fewer cells are required.

The novelty of the present invention is that the adipose tissue is preserved using a specific freezing technology and this during a long period. The unexpected effect of the proposed tissue banking system gives rise to a highly valuable frozen adipose tissue from which different stem and/or progenitor cells can be isolated for therapeutic use or for drug screening or for developing procedures for expansion or differentiation.

The present invention also relates to the commercial provision of the possibility to store the adipose tissue with a sampling method, logistics and preservation technology.

The present invention relates to a method for the cryopreservation of adipose tissue with the intention to use this tissue in the culturing of stem and/or progenitor cells. The method uses a specific cryoprotection medium and a specific cryoprotection method to prevent damage of the original adipose tissue during the cryopreservation.

Cryoprotectants are substances used to protect biological tissue from freezing damage caused by the formation of ice. Cryoprotectants fall into two general categories; permeating cryoprotectants, which can pass through cell membranes, and non-permeating cryoprotectants. Examples of permeating cryoprotectants include, but are not limited to, dimethyl sulfoxide (DMSO), glycerol, sucrose and 1,2-propanediol. Examples of non-permeating cryoprotectant include, but are not limited to, hydroxyethyl starch, albumin, and polyvinyl pyrrolidone. The most commonly employed permeative cryoprotectant is DMSO, which is often used in combination with a non-permeative agent such as autologous plasma, serum albumin, and/or hydroxyethyl starch. By using a mixtures of different cryoprotectants the toxicity of the solution is decreased, hence rendering the solution more effective than single-agent cryoprotectants.

Our inventors found surprisingly that a combination of at least two cryoprotectants chosen from glycerol, serum albumin, sucrose and/or trehalose, provides an ideal medium for the cryopreservation of adipose tissue.

In a first embodiment the composition of the cryoprotection medium for the cryopreservation of adipose tissue is characterized therein that said cryoprotection medium is a solution of physiological water comprising glycerol present in an amount from about 1.6 M to about 2.7 M and sucrose and/or trehalose present in an amount from about 0.1 M to about 0.3 M.

Whereas a skilled person would expect serum albumin to be added to the cryoprotection medium, the inventors have found that serum albumin is not always necessary in the cryoprotection medium for the cryopreservation of adipose tissue. The addition of serum albumin is therefore optional.

In yet another embodiment the cryoprotection medium of the invention is characterized therein that said cryoprotection medium additionally comprises serum albumin in an amount from $1.5 \cdot 10^{-5}$ M to $7.5 \cdot 10^{-4}$ M.

The molar concentrations provided above correspond respectively to glycerol present in an amount from about 15 wt % to about 25 wt %, said sucrose present in an amount from about 4 wt % to about 10 wt % and said serum albumin present in an amount from about 0.1 wt % to about 5 wt %.

A more preferred composition of the cryoprotection medium of the present invention is characterized therein that said glycerol is present in an amount of about 2.2 M, said sucrose and/or trehalose is present in an amount of about 0.2 M and/or said serum albumin in an amount of about $3 \cdot 10^{-4}$ M.

The molar concentrations provided above correspond respectively to glycerol present in an amount of about 20 wt %, said sucrose and/or trehalose present in an amount of about 7 wt % and/or said serum albumin present in an amount from about 2 wt %.

In a more preferred composition the cryoprotection medium of the present invention is characterized therein that said glycerol is present in an amount of about 20 wt %, said sucrose and/or trehalose is present in an amount of about 0.2 M and/or said serum albumin in an amount of about 2 wt %.

The serum albumin in the cryoprotection medium of the present invention refers to human and/or synthetic serum albumin. Due to the health risk associated with the use of xenogeneic sera such as bovine serum albumin, these types of sera are not used in the composition of the present invention. Furthermore, since the method of the invention intents to provide stem and/or progenitor cells for clinical and therapeutical applications, the use of xenogeneic sera in the method is not recommended and should be avoided. Furthermore, since it has already been shown that the presence of xenogeneic sera during cryopreservation can alter the expression profiles and characteristics of the cells, using a cryoprotection medium that is deprived of any xenogeneic sera circumvents these problems.

The present invention also relates to a method for the cryopreservation of adipose tissue, with the intention to use this tissue in the culturing of stem and/or progenitor cells, preferably mesenchymal stem and/or progenitor cells, wherein the method comprises freezing adipose tissue.

In a preferred embodiment of the present invention the adipose tissue is obtained from liposuction aspirates. Liposuction aspirates are considered a waste product from liposuction surgery. During this type of surgery an anaesthetic-containing fluid is injected into the areas containing adipose tissue deposits. The fluid can for instance contain a local anaesthetic such as lidocaine, a drug that constricts blood vessels to reduce blood loss such as epinephrine and a salt solution to allow for easier fat removal. The fluid causes the adipose tissue to swell up and harden, making it easier to remove. Liposuction aspirates are the fluids removed during this type of surgery and comprise beside the adipose tissue also the fluid injected during the surgical procedure. Typically liposuction aspirates contain varying amounts of stem cells, progenitor cells, matrix material, blood, serum, lipids, adipocytes, vascular endothelial cells, vascular smooth muscle cells, and pericytes. The liposuction aspirates include besides the aspirated adipose tissue also other substances such as water, drugs and/or anaesthetics used during the liposuction procedure.

In another preferred embodiment of the present invention the adipose tissue is obtained during surgery.

In a preferred embodiment the present invention relates to a method for the cryopreservation of adipose tissue, comprising the steps of:
a) transporting liposuction aspirate or adipose tissue in a package, container or tube,
b) optionally processing said liposuction aspirate, and extracting adipose tissue,
c) adding a cryoprotection medium according the present invention to said adipose tissue of step a or step b, and,
d) freezing said adipose tissue.

In another preferred embodiment the present invention relates to a method for the cryopreservation of adipose tissue, wherein prior to step a), the liposuction aspirate or adipose tissue is collected after any medical intervention or surgical treatment.

According to the invention, collection of liposuction aspirates can be done by any method known in the art. For example, liposuction aspirates may be collected during various routine liposuction procedures such as performed for the purpose of aesthetic body recontouring. The liposuction aspirates can be collected into a device designed for and dedicated to the purpose of collecting the liposuction aspirates for banking or it can be collected into the usual devices used for collection of liposuction aspirates by personnel performing liposuction procedures. The collection of liposuction aspirates is preferably made under sterile conditions.

During the collection of the liposuction aspirates the pressure at the pump should not increase the 15 mm Hg in order to maintain the viability of the aspirated cells.

In a first embodiment, at least 10 ml, preferably at least 25 ml and more preferably at least 50 ml of liposuction aspirate is obtained. However, smaller and larger amounts of liposuction aspirate may also be acceptable, and indicated under some circumstances. For example, it may be acceptable or preferable to harvest larger amounts of adipose tissue from obese or overweight individuals than from lean persons.

Immediately after collection, the liposuction aspirates and/or collection device should be sealed and transported to a processing facility within a period of maximum 24 hours. In case the period between the collection and the processing of the liposuction aspirate exceeds 24 hours the viability of the stem and/or progenitor cells obtained from cryopreserved adipose tissue reduces. It is anticipated that, in some settings, the collection facility and the processing facility may be in close proximity permitting a simplified sealing and transportation of the product from one area to another.

Preferably the adipose tissue is transported in a leak proof container to the processing laboratory within 48 hours after collection. Preferably, the temperature of transport may not exceed 25° C. to avoid contamination.

According to the present invention, the liposuction aspirates are further processed. Upon arrival in the processing laboratory, the liposuction aspirate solution is equilibrated for a period of approximately 30 minutes until three phases are formed: an oil layer, a processed lipoaspirate or adipose tissue fraction and a liposuction aspirate fluid fraction. From these fractions the adipose tissue is extracted. In a preferred embodiment according to the method of the invention, the adipose tissue is extracted from the liposuction aspirate during the processing step. Preferably at least 1 ml of the adipose tissue is extracted, more preferably at least 5 ml, more preferably at least 7.5 ml and most preferably 10 ml or at least 10 ml of the adipose tissue is extracted. However, smaller and larger amounts of adipose tissue may also be extracted depending on the amount of liposuction aspirate and the dilution thereof.

During this processing step an optional quality control of the adipose tissue can be performed. During this step the sterility of the adipose tissue is preferably monitored. This is for instance done by filtering the adipose tissue through a Millipore filter with a pore size of 0.45 micrometer and subsequently culture the filter on an agar plate. When no contamination is found after culturing the filter during 2 weeks on an agar plate, the culture is considered sterile.

In a preferred embodiment the invention relates to a method of the invention, wherein the cryoprotection medium of step (c) is a solution of physiological water comprising glycerol, sucrose and/or serum albumin, glycerol is preferably present in an amount from about 15 wt % to about 25 wt % and more preferably about 20 wt %, sucrose is preferably present in an amount from about 4 wt % to about 10 wt % and more preferably about 0.2 M and/or serum albumin is preferably present in an amount from about 0.1 wt% to about 5 wt % and more preferably about 2 wt %.

According to the present invention, equal amounts of cryoprotection medium and adipose tissue are required for ideal cryopreservation. Preferably a volume of the cryoprotection medium ranging between 5 ml and 50 ml is mixed with an equal amount of adipose tissue. In a more preferred embodiment, the volume ranges between 5 and 25 ml, more preferably between 5 and 15 ml and for instance 10 ml of cryoprotection medium is added to 10 ml of adipose tissue.

However, smaller and larger amounts of cryoprotection medium and adipose tissue may also be acceptable. Therefore, in yet another embodiment according to the present invention, a volume of the cryoprotection medium up to 1000 ml or up to 2000 ml is mixed with an equal amount of adipose tissue.

In a preferred embodiment of the present invention, the volume ratio of adipose tissue to cryoprotection medium ranges between 2:1 and 1:2. More preferably the volume ratio is approximately 1:1.

In a preferred embodiment the volume ratio of adipose tissue to cryoprotection medium is 1:1. Consequently to a volume ratio of 1:1, the cryoprotection medium as referred to in the present application is twice the concentration of the components in the medium after addition of the adipose tissue. The cryoprotection medium can consequently be defined as a 2× cryoprotection medium.

In yet another embodiment, the inventors have found that the concentration of the components of the cryoprotection medium can be increased up till 3, 4, 5, 6, 7 or 8 times the concentration of the components in the medium after addition of the adipose tissue or 1.5, 2, 2.5, 3, 3.5 or 4 times the concentration of the cryoprotection medium. These concentrated cryoprotection media can consequently be defined as respectively a 3×, 4×, 5×, 6×, 7× or 8× concentrated cryoprotection medium. It has been found that the concentrated cryoprotection media do not alter the characteristics of said medium upon freezing. Preferably when using a 3×, 4×, 5×, 6×, 7× or 8× concentrated cryoprotection medium the volume ratio of adipose tissue to concentrated cryoprotection medium is respectively approximately 2:1, 3:1, 4:1, 5:1, 6:1 or 7:1. With respect to the cryoprotection medium, the 3×, 4×, 5×, 6×, 7× or 8× concentrated cryoprotection media have a concentration which is respectively 1.5, 2, 2.5, 3, 3.5 or 4 times the concentration of the cryoprotection medium according to the present invention.

In a preferred embodiment, the present invention regards a concentrated cryoprotection medium, characterized therein that said concentrated cryoprotection medium provides a concentration that is 1.5, 2, 2.5, 3, 3.5 or 4 times the concentration of the cryoprotection medium according to the present invention.

In a more preferred embodiment, the present invention regards a concentrated 5× cryoprotection medium wherein the volume ratio of adipose tissue to cryoprotection medium is approximately 4:1.

Accordingly, in another embodiment the present invention relates to a frozen medium comprising adipose tissue and cryoprotection medium, characterized therein that said frozen medium comprises glycerol in an amount from 0.8 M to 1.35 M, sucrose and/or trehalose in an amount from 0.05 M to 0.15 M. More preferably the frozen medium comprises serum albumin in an amount from $0.75 \cdot 10^{-5}$ M to $3.75 \cdot 10^{-4}$ M.

According to the present invention the frozen medium refers to the composition obtained by mixing the cryoprotection medium and the adipose tissue.

According to the present invention, the cryoprotection medium is cooled to approximately 4° C. prior to adding to the adipose tissue. In a preferred embodiment said cryoprotection medium is pre-incubated at approximately 4° C. prior to adding to the adipose tissue for at least 15 minutes, preferably at least 30 minutes and more preferably at least 60 minutes.

After addition of the cryoprotection medium two cryopreservation methods can be applied for the freezing of the adipose tissue.

In a slow freezing method the adipose tissue is cryopreserved in a container, preferably a collection bag also called flat bag. These flat bags typically have low volumes of less than 100 ml, preferably less than 50 ml and for instance 25 ml. Equal amounts of the adipose tissue and the cryoprotection medium, preferably cooled to approximately 4° C., are mixed in a flat bag. Before sealing the bag, air is removed from the bag. The flat bags are subsequently gradually cooled down to about −45° C. The flat bags are frozen with a slow cooling rate of ranging between about −0.1° C. and about −5° C. per minute, preferably between about −0.5° C. and about −2° C. per minute and for instance about −1° C. per minute. Subsequently the bags are transferred to a temperature of at least −80° C., preferably at least −100° C., more preferably at least −150° C. and for instance into the vapour phase of liquid nitrogen at approximately −196° C. Although, the slow freezing method can be performed on adipose tissue in any type of container, the inventors have found that cryopreserving adipose tissue in flat bags considerably improves the viability of the stem and/or progenitor cells obtained from cryopreserved adipose tissue. The specific combination of flat bags and a specific cryoprotection medium enables the long term storage of the adipose tissue. The use of flat bags as storage system enhances the contact surface of the adipose tissue solution which has a beneficial effect on the cryopreservation and subsequent isolation of stem and/or progenitor cells from the cryopreserved adipose tissue.

In a fast freezing or vitrification method the adipose tissue is cryopreserved in any type of container. When choosing a suitable container for fast freezing or vitrification care has to be taken that the surface to volume ratio is optimal to provide an equal freezing of the entire solution. Also the vitrification method needs to be performed using a system that provides enough freezing capacity to obtain ideal freezing conditions. The container is subsequently put at a temperature of at least −80° C., preferably at least −100° C., more preferably at least −150° C. and for instance into the vapour phase of liquid nitrogen at approximately −196° C.

In a preferred embodiment the invention relates to a method of the invention, wherein the freezing method of step (e) is a slow freezing method. In a preferred embodiment said slow freezing method cools the adipose tissue to about −45° C. at a cooling rate ranging between about −0.1° C. and about −5° C. per minute, preferably between about −0.5° C. and about −2° C. per minute and for instance about −1° C. per minute and the adipose tissue is subsequently incubated at a temperature of at least −80° C., preferably at least −100° C., more preferably at least −150° C. and for instance at approximately −196° C. In another preferred embodiment the slow freezing method is performed by means of a flat bag.

In another preferred embodiment the invention relates to a method of the invention, wherein the freezing method of step (e) is a vitrification method. More preferably said vitrification method cools the adipose tissue to a temperature of at least −80° C., preferably at least −100° C., more preferably at least −150° C. and for instance at approximately −196° C. The cooling rate of the vitrification method ranges between about −20° C. and about −80° C. per minute, preferably between about −40° C. and about −60° C. per minute and for instance about −50° C. per minute.

The adipose tissue can remain in a cryogenic state for long periods of days, weeks, months or years, for retrieval when a source of stem and/or progenitor cells is required. When required, the cryopreserved adipose tissue is retrieved and thawed. The container containing the adipose tissue can for instance be thawed in a bath of warm water, at a temperature of maximum 40° C., preferably between 10° C. and 40° C. and for instance about 37° C. To reduce the mechanical destruction of the tissue and preserve the postthaw cell viability a thawing rate between about 10° C. and about 40° C. per minute, preferably between about 20° C. and about 40° C. per minute and for instance approximately 30° C. per minute is used.

In another embodiment the invention relates to a method of the invention, wherein the method further comprises a step to thaw said adipose tissue. Preferably the thawing of said adipose tissue is performed in a bath of warm water, at a temperature of maximum 40° C., preferably between 10° C. and 40° C. and for instance about 37° C. Preferably the thawing of said adipose tissue is performed at a quick thawing rate between about 10° C. and about 40° C. per minute, preferably between about 20° C. and about 40° C. per minute and more preferably a quick thawing rate of approximately 30° C. per minute.

After thawing the cryopreserved adipose tissue stem and/or progenitor cells can be isolated using conventional and published methods known by a person skilled in the art. These methods first include an isolation of the adipose tissue and a removal of the cryopreservation medium by several sequential centrifugation and washing steps followed by the subcultivation of the stem and/or progenitor cells.

Therefore, in a further embodiment of the present invention the method of the present invention further comprises the steps to thaw said adipose tissue and steps allowing that after thawing stem and/or progenitor cells are recovered from said adipose tissue.

At this point in the process the quality of the culture can be monitored. Several controls can be performed such as a sterility control, immunophenotype characterisation, differentiation tests and an inspection of the morphology of the stem and/or progenitor cells.

The sterility of the stem and/or progenitor cell culture is monitored. This is for instance done by filtering the culture through a filter with a pore size of 0.22 micrometer and subsequently culture the filter on an agar plate. When no contamination is found after culturing the filter during 2 weeks on an agar plate, the culture is considered sterile.

The characterisation of the immunophenotype of the stem and/or progenitor cells is done by flow cytometry analysis. During this analysis specific markers on the surface of the stem and/or progenitor cells are detected and analysed.

In another type of quality control, the obtained stem and/or progenitor cells are tested on their differentiation capacity. This is a standard test to identify the capacity of the stem and/or progenitor cells for differentiation to osteoblast, adipocyte and chondroblast using an in vitro tissue culture condition test.

The morphology of the stem and/or progenitor cells is visually inspected using techniques known in the art. Based on the morphology of the stem and/or progenitor cells a skilled person is able to assess the quality of the stem and/or progenitor cells.

The method of the present invention provides a viability of the stem and/or progenitor cells after thawing and further processing of at least 50% and preferably more than 70% viability. These cells can be used as primary explant in different cellular therapy applications.

In another embodiment of the present invention stem and/or progenitor cells may be isolated after the thawing of said adipose tissue.

In another embodiment the invention relates to a method for the isolation of stem and/or progenitor cells from adipose tissue cryopreserved according to a method of the invention. The inventors found surprisingly that by using the method of the present invention the viability of the recovered stem and/or progenitor cells is at least 50%, preferably at least 70%, more preferably at least 80% and for instance 80%, 81%, 82%, 83%, 84%, 85%, 86%, 87%, 88%, 89%, 90%, 91%, 92%, 93%, 94%, 95%, 96%, 97%, 98%, 99% or 100%.

A consequence of the high viability of the recovered stem and/or progenitor cells is that the present invention provides a method for obtaining a large amount of stem and/or progenitor cells from cryopreserved adipose tissue. At least 10 million viable stem and/or progenitor cells are obtained from the cryopreserved adipose tissue after culturing, preferably the amount is more than 50 million and more preferably more than 100 million. The high amount of stem and/or progenitor cells obtained from the cryopreserved adipose tissue provides an ideal dose for medical use of the obtained stem and/or progenitor cells.

In a particular embodiment of the present invention the stem and/or progenitor cells isolated from the cryopreserved adipose tissue may be cryopreserved using known stem and/or progenitor cell cryopreservation techniques.

The stem and/or progenitor cells referred to in the present invention may be chosen from the group consisting of mesenchymal stem and/or progenitor cells, endothelial stem and/or progenitor cells, epithelial stem and/or progenitor cells and muscle stem and/or progenitor cells, preferably mesenchymal stem and/or progenitor cells.

The present invention further relates to highly viable stem and/or progenitor cells obtained from adipose tissue that has been cryopreserved according to a method of the invention. More preferably said stem and/or progenitor cells may be chosen from the group consisting of mesenchymal stem and/or progenitor cells, endothelial stem and/or progenitor cells, epithelial stem and/or progenitor cells and muscle stem and/or progenitor cells, and more preferably mesenchymal stem and/or progenitor cells.

The present invention also relates to stem and/or progenitor cells obtained from adipose tissue cryopreserved according to a method of the invention for the use in medicine, preferably regenerative medicine.

It should be noted that it is commonly known in the art that stem and/or progenitor cells upon being treated for cryopreservation, undergo a number of genetic and/or proteomic changes. The more procedural treatment steps stem and/or progenitor cells undergo, the more profound the effects of these treatment steps will be on the stem and/or progenitor cells obtained after preservation. The method according to the present invention minimizes the number of procedural treatment steps, especially since the adipose tissue itself is cryopreserved, whereas is method according to the prior art stem and/or progenitor cells need to be collected prior to cryopreservation. The reduced number of procedural steps in the method according to the present invention consequently reduces the genetic and/or proteomic changes in the stem and/or progenitor cells obtained after cryopreservation.

In another embodiment the present invention relates to a biological or pharmaceutical composition comprising stem and/or progenitor cells according to the above.

The present invention further relates to an adipose tissue cryopreserved according to the method of the present invention. According to the present invention, said cryopreserved adipose tissue may be used for the preparation of highly viable stem and/or progenitor cells or for the preparation of a therapeutic cells or a medicament.

The present also contemplates stem and/or progenitor cells recovered or obtained by a method of the present invention or a use according to the invention. Biological or pharmaceutical compositions can be prepared comprising said stem and/or progenitor cells.

Furthermore, according to the present invention the stem and/or progenitor cells or the biological or pharmaceutical composition described above may be used for the preparation of therapeutic cells or a medicament for the treatment of a disorder or a disease, or, a predisposition of a disorder or a disease. In particular, said stem and/or progenitor cells or a biological or pharmaceutical composition may be used for the preparation of a replacement or engineered tissue, graft or transplant. Said replacement may be an allogenic replacement or an autologous replacement. The disease or disorder referred to in the present application may be chosen from the group consisting of diabetes, neoplastic diseases, skin diseases, metabolic and neurological disorders, bone defects, osteoporosis, myocardial infarction, bone fracture, cartilage damage through accident or arthritis, neurological damage or disease, vascular ischemia, coronary artery disease, chronic skin wounds, osteogenesis imperfecta, and aesthetic or trauma related plastic surgical applications.

The method of the present invention can also be used to provide stem and/or progenitor cells from cryopreserved adipose tissue for use as local implantations. The local implantation of stem and/or progenitor cells can for instance be used for a faster and more effective healing of bone defects, the repair of cartilage damage, vascular ischemia, coronary artery disease, chronic skin wounds or myocard infarcts.

The method of the present invention can also be used to provide stem and/or progenitor cells from cryopreserved adipose tissue for use in tissue engineering. In tissue engineering stem and/or progenitor cells can be combined with suitable biochemical and physio-chemical factors to improve or replace biological functions. Certain portions or whole tissues can be repaired or replaced using tissue engineering.

Moreover, the method of the present invention can be used to provide stem and/or progenitor cells from cryopreserved adipose tissue for use in and differentiation into different type of tissues such as bone fat and cartilage for tissue repair and systemic transplantations, osteogenesis imperfecta or treatment of bone defects, haematopoietic co-transplantation to accelerate the reconstitution of haematopoiesis. Furthermore, the method of the present invention can be used to provide stem and/or progenitor cells from cryopreserved adipose tissue for use in mesenchymal stem cell transplantation where purified stem cells are used for grafting or in cardiac regeneration and lung repair. The method of the present invention can also be used to provide stem and/or progenitor cells from cryopreserved adipose tissue for use as a tool in gene therapy.

The method of the present invention can also be used to provide stem and/or progenitor cells from cryopreserved adipose tissue for use in the treatment of heart disease. For the treatment of heart disease several clinical trials have already shown that adult stem cell therapy is safe and effective.

Finally, the method of the present invention can be used to provide stem and/or progenitor cells from cryopreserved adipose tissue for use in the treatment of diabetes. Since mesenchymal stem cells can differentiate into pancreatic insulin producing islet cells, the functionality of these cells can be regenerated.

In a preferred embodiment the present invention therefore relates to stem and/or progenitor cells obtained from adipose tissue cryopreserved according to the method of the present invention, wherein the obtained stem and/or progenitor cells are used in the manufacturing of a medicament, and preferably a medicament for regenerative medical applications.

In another preferred embodiment the present invention relates to stem and/or progenitor cells obtained from adipose tissue cryopreserved according to the method of the present invention, or a biological or pharmaceutical composition according to the present invention, wherein said stem and/or progenitor cells or said composition are used in the manufacturing of a medicament for the treatment of a disorder or a disease, or, a predisposition of a disorder or a disease, wherein said disease or disorder may preferably be chosen from the group consisting of diabetes, neoplastic diseases, skin diseases, metabolic and neurological disorders.

In yet another preferred embodiment the present invention relates to stem and/or progenitor cells obtained from adipose tissue cryopreserved according to the method of the present invention, or a biological or pharmaceutical composition according to the present invention, wherein said stem and/or progenitor cells or said composition are used in the manufacturing of a medicament for the preparation of a replacement or bio-engineered tissue, graft or transplant.

Stem and progenitor cells which contain a heterologous gene sequence for use in gene therapy in delivering replacement or novel gene sequences is also contemplated.

The invention also contemplates a plurality of viable stem and/or progenitor cells stored through the cryopreservation system for future use in methods to prepare cell transplants, to prepare bio-engineer organ parts or even organs (e.g. nerve bundles for spinal cord repair, liver pancreas), to rebuild cartilage after sport injuries, accidents, surgery on joints or arthrosis, to repair tissue for cosmetic and reconstructive surgery, repair in skin from burns or to prepare cells which can be used in gene-therapeutic applications (e.g. cancers, cystic fibrosis, Huntington disease, Thalassaemia, Hemophilia . . . ). At this moment different protocols exist to generate differentiated cells for tissue repair.

Diseases that potentially could be cured are increasing: different types of carcinomas and other neoplastic diseases, skin diseases (wound and burn healing), metabolic diseases (diabetes or other hormone deficiencies) and neurodegenerative diseases (Alzheimer, Parkinson, multiple sclerosis . . . ).

The present invention also relates to the pharmacological composition comprising the stem and/or progenitor cells recovered or prepared according to a method or use of the present invention and optionally may further comprise a pharmaceutical acceptable carrier, diluent or excipient. More preferably said stem and/or progenitor cells may be chosen from the group consisting of mesenchymal stem and/or progenitor cells, endothelial stem and/or progenitor cells, epithelial stem and/or progenitor cells and muscle stem and/or progenitor cells, and more preferably mesenchymal stem and/or progenitor cells.

In another embodiment the present invention further contemplates a kit for the cryopreservation of an adipose tissue comprising:
a. a (set of) container(s), package(s) or tube(s) to cryopreserve adipose tissue(s),
b. information on how the collection of the adipose tissue during surgery should be performed,
c. logistic information on how samples should be transported, preferably within the time frame of 24 hours and indications on temperature, packaging, and tracking, The present invention also relates to a storage processing service using a method described above to insure the possibility to treat certain abnormalities, disorders, dysfunctions or diseases, using stem cell technology.

The present invention provides an easy method to store adipose tissue with the intention to isolate a high yield of different type of stem and/or progenitor cells in an efficient and preferably large scale technological approach. In this way, various stem and/or progenitor cells are preserved for future use. Based on the method of the present invention, an unlimited supply of progenitor cells can be saved for future regenerative therapeutic use in different tissue repair set up.

It is to be understood that while the invention has been described in conjunction with the detailed description thereof, the foregoing description is intended to illustrate and not limit the scope of the invention, which is defined by the scope of the appended claims.

EXAMPLES

Example 1

Cryopreservation of Adipose Tissue: Slow Freezing Procedure

The present invention relates to a method for storing adipose tissue cryogenically using the following exemplified procedure.

During liposuction surgery at least 50 ml liposuction aspirate is collected and within 24 hours the collected fluid is transported to the processing laboratory. Upon arrival in the processing laboratory, the liposuction aspirate solution is equilibrated for a period of approximately 30 minutes until three phases are formed: an oil layer, a processed lipoaspirate or adipose tissue fraction and a liposuction aspirate fluid fraction. From these fractions the adipose tissue is extracted. A small collection bag of 25 ml, also called flat bag, is filled with 10 ml of the adipose tissue and 10 ml of the cryoprotection medium cooled at a temperature of 4° C. The cryoprotection medium is a solution of physiologic water containing 20 wt % glycerol, 0.2 M sucrose and 2 wt % serum albumin. After pooling both solutions in the bag, air is removed from the bag and the bag is sealed. The flat bag is subsequently placed in a gradual freezing machine to cool it down. The fat bags are frozen with a slow cooling rate of 1° C. per minute from 4° C. to −45° C. The flat bags are then immediately transferred into the vapour phase of liquid nitrogen at −196° C. for long term storage.

Example 2

Cryopreservation of Adipose Tissue: Vitrification Procedure

The present invention relates to a method for storing adipose tissue cryogenically using the following exemplified procedure.

The collection, transport and processing of the liposuction aspirate is identical to the procedure described in example 1. After extracting the adipose tissue, a small collection bag of 25 ml, also called flat bag, or tube is filled with 10 ml of the adipose tissue and 10 ml of the cryoprotection medium cooled at a temperature of 4° C. The cryoprotection medium is a solution of physiologic water containing 20 wt % glycerol, 0.2 M sucrose and 2 wt % serum albumin. After pooling both solutions in the tube or bag (air is removed from the bag and the bag is sealed), it is immediately transferred into the vapour phase of liquid nitrogen at −196° C. for long term storage.

Example 3

Isolation of Mesenchymal Stem Cells From Cryopreserved Adipose Tissue

The present invention relates to the isolation of stem and/or progenitor cells from adipose tissue that has been stored cryogenically using the following exemplified procedure.

Adipose tissue cryopreserved using methods of the present invention and as illustrated in examples 1 and 2 is thawed by removing the tube or bag from the liquid nitrogen storage facility. The tube or bag is immediately placed into a water bath at 37° C. Once fully thawed the adipose tissue is centrifuged at low velocity (50 g) for a time interval of 2 minutes. Two fractions appear: a bottom fraction with the cryoprotection medium and an upper fraction being the adipose tissue. The adipose tissue is added to 8 ml of phosphate-buffered saline (PBS) without calcium (1× GIBCO 14190) and 2 mL collagenase type I of 0.75 wt %. The solution is mixed in a tube and incubated in a water bath at 37° C. for 30 minutes. Afterwards the tube is centrifuged for 10 minutes at 800 g and the supernatant is removed. 5 ml of a culture medium containing DMEM and 15% fetal bovine serum and 100 IU µg/ml Penicilline/Streptomycine is added to the tube and the pellet is suspended. In a next step the cell suspension is passed through a 40 micrometer mesh filter and it is added to a culture flask filled with 10 ml of the culture medium. The flask is put in an incubator at 37° C., 5% $CO_2$ and 100% humidity for 1 day.

The next day the culture medium is removed from the flask using a 25 mL serological pipette without damaging the attached cells, the flask is washed 2 times with 5 ml PBS without calcium and 15 ml of fresh culture medium is added to the flask. The flask is incubated at 37° C. and 5% $CO_2$, and 100% humidity. The refreshment of the culture medium is done every 3 days until 80% confluency is reached.

Once 80% confluency is reached the culture medium is removed from the flask and the cell area is washed twice with PBS deprived of Calcium. Subsequently the adherent cells are detached with a 0.25% trypsin 1 mM EDTA solution and replated at a density of minimum 500 cells per $cm^2$ until further processing. At this moment in the procedure a cell count and viability test is done with Tryptan blue. The minimum viability obtained with this procedure is 70% and a cell count of $10^6$ cells per ml is reached. These values for viability and cell count are ideal for the use of these cultured mesenchymal stem cells in medicine.

Example 4

Sterility Control

During the culturing procedure of the mesenchymal stem cells the sterility of the culture can be controlled. This can for instance be performed by checking the sterility of the removed medium by filtering this medium through a Millipore filter with a pore size of 0.45 micrometer and culturing the filter on an agar plate during 2 weeks. If no contamination is observed during these two weeks the culture is considered sterile.

Example 5

Immunophenotype Characterisation

The isolated mesenchymal stem cells can be characterised with flow cytometric analysis techniques (FACS) since mesenchymal stem cells express matrix receptors CD44, CD105, CD90 and CD105 but not the haematopoietic lineage markers CD34 and CD45.

For FACS analysis $10^5$ cells isolated from adipose tissue were stained with phycoerythrin-conjugated antibodies against CD45 and CD73, or fluorescein isothiocyanate-conjugated antibodies against CD44. Monoclonal antibodies served as the control.

Analysis by flow cytometry with a FACScan showed that the mesenchymal stem cells obtained from cryopreserved adipose tissue demonstrated a fibroblast-like phenotype. Flow cytometric analysis showed that the cells expressed high levels of matrix markers CD44 and CD73, but did not express haematopoietic lineage markers CD34 and CD45.

This analysis clearly shows that the cells isolated from cryopreserved adipose tissue are mesenchymal stem cells.

Example 6

Differentiation Tests

Differentiation tests are in vitro tissue culture condition tests that can be performed on mesenchymal stem cell lines to assess the capacity of the cells to differentiate into osteoblasts, adipocysts and chondroblasts.

Differentiation tests on mesenchymal stem cells isolated according to methods of the present invention and as illustrated in example 3 showed the capacity to differentiate into these three types of cells. Furthermore the isolated mesenchymal stem cells also showed the capacity to differentiate into osteogenic and adipogenic cells under suitable culture conditions.

The invention claimed is:

1. A method for the cryopreservation of adipose tissue, comprising the steps of:
   a) transporting liposuction aspirate or adipose tissue in a package, container or tube,
   b) optionally processing said liposuction aspirate, and extracting adipose tissue,
   c) adding a cryoprotection medium comprising a solution of aqueous saline solution comprising glycerol in an amount from 1.6 M to 2.7 M and sucrose in an amount from 0.1 M to 0.3 M to adipose tissue of step a or step b, and,
   d) cryopreservinq said adipose tissue,
   wherein said cryoprotection medium further comprises serum albumin in an amount from $1.5 \times 10^{-5}$ M to $7.5 \times 10^{-4}$ M.

2. The method according to claim 1, wherein the volume ratio of adipose tissue to cryoprotection medium ranges between 2:1 and 1:2.

3. The method according to claim 2, wherein said adipose tissue is cryopreserved using a vitrification method.

4. The method according to claim 1, wherein said adipose tissue is cryopreserved using a vitrification method.

5. The method according to claim 1, wherein the volume ratio of adipose tissue to cryoprotection medium is approximately 1:1.

* * * * *